United States Patent
Kobayashi

Patent Number: 5,897,591
Date of Patent: Apr. 27, 1999

[54] IMPLANT FOR INJURED TENDON OF DIGITUS MANUS

[76] Inventor: Masanori Kobayashi, 7-5, Goryo Ikenotani, Nishikyo-ku Kyoto-shi, Kyoto 615, Japan

[21] Appl. No.: 09/003,601

[22] Filed: Jan. 7, 1998

[30] Foreign Application Priority Data

Jan. 20, 1997 [JP] Japan ...................................... 9-007126

[51] Int. Cl.$^6$ .................................................. A61F 2/08
[52] U.S. Cl. ............................................. 623/13; 606/151
[58] Field of Search ................................. 623/13, 11, 12; 606/151, 152; 600/37

[56] References Cited

U.S. PATENT DOCUMENTS

| | | | |
|---|---|---|---|
| 3,842,441 | 10/1974 | Kaiser ........................................ | 623/13 |
| 4,400,833 | 8/1983 | Kurland ..................................... | 623/13 |
| 4,753,652 | 6/1988 | Langer et al. .............................. | 623/1 |
| 5,012,503 | 4/1991 | Nambu et al. ............................. | 378/64 |
| 5,458,636 | 10/1995 | Brancato ................................... | 623/13 |
| 5,480,427 | 1/1996 | Kelman et al. ............................. | 623/6 |
| 5,700,583 | 12/1997 | Jamiolkowski et al. ................. | 428/482 |

FOREIGN PATENT DOCUMENTS 1-124464  5/1989  Japan .

*Primary Examiner*—Mickey Yu
*Assistant Examiner*—Bruce E. Snow
*Attorney, Agent, or Firm*—Banner & Witcoff, Ltd.

[57] ABSTRACT

An implant for an injured tendon of a digitus manus having a tube-shaped body with obliquely angled opposite ends made of a macromolecule polyvinyl alcohol family having characteristics of a long life to a living organism and a low reactivity to a foreign body, for example, macromolecule polyvinyl alcohol hydrogel. An injured tendon of a digitus manus is inserted into and passed through inside of the implant so as to function for suture and cure of the injured tendon, and for convalescence such as preventing the sutured tendon from coalescing with its ambient living organism. More specifically, since the sutured portion of the tendon is inserted into and surrounded by the implant, coalescence of the sutured portion of the tendon with the ambient skin is prevented and soft tissue does not get hurt because of the moisture contents of the implant, thereby to avoid dysfunction.

6 Claims, 7 Drawing Sheets

Exposure of Peripheral Tendon and Suture of Tendon

Fig. 7

Needle for Fixing Tendon     Incise Tendon Supplementary If Necessary

Related art

Related art

IMPLANT FOR INJURED TENDON OF DIGITUS MANUS

BACKGROUND OF THE INVENTION

1. Field of the Invention

This invention relates to an implant for an injured tendon of a digitus manus into inside of which an injured tendon of a digitus manus is inserted and passed through so as to function for suture and cure of the injured tendon, and for convalescence such as preventing the sutured tendon from coalescing with a living organism surrounding the sutured tendon.

2. Discussion of the Relevant Art

Tendon injuries (cut off or damaged) of a digitus manus happens daily such as during working or exercising although a degree of the injuries varies. When a tendon of a digitus manus is injured, basically it is important to treat, namely, to suture the injured tendon as fast as possible after getting injured. And this primary treatment will affect greatly on its convalescence. During the process of healing not only the amputated tendon conglutinates but also the sutured portion of the tendon coalesces with its ambient tissue of the living organism, thereby to bring about dysfunction. This makes it difficult to conduct an operation to suture an injured tendon. The injury of a flexor tendon, especially a portion called "the Zone 2" is a top problem to be solved.

With the recent progress of the orthopaedic surgery, various methods of suturing operation have been studied and developed as shown in FIGS. 10 and 11. More concretely, as a conventional method of suturing operation there is Verdon's suture method (FIG. 10A). This method is to make both ends K1, K2 of an amputated tendon abutting contact with each other and to suture several points around the abutting contact face. A method for more steady suture is Kieinert's suture method (FIG. 10B). This method is to cross a stitch to suture both ends K1, K2 of the amputated tendon. Bunuell's suture method shown in FIG. 10C is to make both ends K1, K2 of the amputated tendon abutting contact with each other, to suture the amputated tendon with a stitch penetrating through two points of upper and under of the center of the abutting contact face perpendicularly, and to cross the stitch like the above-mentioned Kieinert's suture method with both ends of the stitch gathered to one side of the tendon. There are other methods such as Kessler's suture method (FIG. 10D), modified Kessler's suture method (FIG. 11A), Tajima's suture method (FIG. 11B), Pennington's suture method (FIG. 1C) and Becker's suture method (FIG. 1D). Kessler's suture method is similar to Bunuell's suture method except a stitch is not crossed but turned to form a loop. Modified Kessler's suture method is a simplified version of Kessler's suture method. Tajima's suture method is to make both ends K1, K2 of the amputated tendon abutting contact with each other and to suture the tendon with a pair of stitches bound to form a loop inside the tendon with one of the stitches penetrating through the upper point of the center of the abutting contact face perpendicularly and the other penetrating through the under point of the center of the contact face perpendicularly. Pennington's suture method is the same as Kessler's except both ends of a stitch are located on the contact face. Becker's suture method is to overlap each of the ends K1, K2 of the amputated tendon along a longitudinal direction thereof in a given length and to suture the amputated tendon in a given area with a stitch crossed along a longitudinal direction. Becker's suture method is the most reliable for suturing an amputated tendon, however, it takes time. As mentioned above, convalescence after tendon injury has been far improved because of the suturing methods having been developed and devised, however, highly advanced techniques and procedures are still required for an operation of tendon injury. Therefore, tendon injury is still one of the most difficult cases to operate for general surgeons. It has been well-known that an operation of a tendon is difficult, but there is another factor which makes the operation of a tendon difficult. The factor is the sutured portion of the tendon coalesces with its ambient tissue of living organism. Coalescence occurs most of the cases in the process of curing injury regardless of the force by which a tendon is injured, namely, a dull force or a keen knife. If coalescence occurs, the movement of the sutured portion of the tendon is restricted even if the injured portion of the tendon has been cured, thereby to bring about dysfunction.

The above-mentioned surgical procedures are primary intended to minimize coalescence. In order to attain the above-mentioned object various suture methods, surgical apparatus, or materials of a stitch which can prevent coalescence have been developed, improved or suggested. Concretely, several procedures of suturing a tendon have been improved for a primary suture operation. Further procedures of grafting a tendon have been improved, devised for a secondary suture surgery or reconstructive surgery. A method of covering an injured tendon with a material whose primary ingredient is a copolymer of amino acid and polyurethane, a method of covering an injured tendon with the material shaped into a tube (Japanese Patent Laid Open Number 1-124464 "Membrane to prevent coalescence") and a method of wrapping an injured tendon with the material have been suggested.

As mentioned above surgery of a tendon is considered to be difficult. However, treatment and convalescence of injuries of a tendon of a digitus manus have been improved because suture methods, surgical apparatus, or materials of a stitch to prevent coalescence have been developed, improved or suggested. In order to further improve a method of tendon surgery a material which can perfectly prevent coalescence is to be established and the surgery should be conducted by a surgeon of a hand specialist or a fully experienced orthopaedic surgeon who has enough knowledge of the material to prevent coalescence. However, it happens so often that a tendon of a digitus manus gets some injury that all of the cases of injury can not be treated by a fully experienced surgeon. In addition to this, a material which can perfectly prevent coalescence has not yet been established. As a result of this, there are not a few cases that dysfunction is caused after the injury has been cured or that reoperation treatment is required due to unsuitable primary treatment just after injury.

It is an object of the present invention to provide an implant for an injured tendon of a digitus manus which can solve the above-mentioned problem. More specifically, the characteristic of the implant in accordance with the present claimed invention is the material of which the implant is made.

SUMMARY OF THE INVENTION

To accomplish the above-mentioned object the invention has adopted the following structure. An implant for an injured tendon of a digitus manus in accordance with the invention comprises a tube-shaped body made of a macro-molecule polyvinyl alcohol family having characteristics of a long life to a living organism and a low reactivity to a foreign body. An injured tendon of a digitus manus is inserted into and passed through inside of the implant so as to function for suture and cure of the injured tendon, and for convalescence such as to prevent the sutured tendon from coalescing with its ambient living organism.

Since the implant is made of the material having characteristics of a long life to a living organism and a low reactivity to a foreign body, coalescence of the sutured tendon with its ambient tissue is prevented.

As mentioned above, the implant in accordance with the invention is made of a macromolecule polyvinyl alcohol family which has characteristics of a long life to a living organism and a low reactivity to a foreign body so that a sutured portion of the injured tendon of a digitus manus does not coalesce with its ambient tissue of living organism even after the digitus manus is fixed for a long time. In addition, soft tissue around the sutured portion does not get damage because of the moisture content of the implant. Dysfunction will not be caused by the implant. The function of the digitus manus is not hindered by the implant. The implant can also be withdrawn after the injured tendon is recovered. If a secondary treatment is required because a sutured tendon fails to recover satisfactory, it is easy to conduct a secondary operation such as a tendon grafting because the sutured portion of the injured tendon does not coalesce with its ambient tissue of living organism. In addition, due to the characteristics of the material the implant is made, a suitable primary treatment to prevent coalescence can be provided without a surgeon of a hand specialist or an experienced orthopaedic surgeon, thereby to promote prognostic cure. A mechanism of reproduction or repair of a tendon has not been determined yet in spite of a lot of researches, however, it is considered that both of blood circulation from the center of the tendon and synovia from the surface layer of the tendon are required. Therefore, a special surgical process is required for suture of an injured tendon (especially, a primary suture of an flexor tendon) to keep the above functions, namely blood circulation and synovia. The implant of the present claimed invention is useful because it is easy to be fixed and it does not hinder both of the functions.

DESCRIPTION OF THE PREFERRED EMBODIMENT

An embodiment of the invention will now be described below with reference to figures.

Figures 1A, 1B:
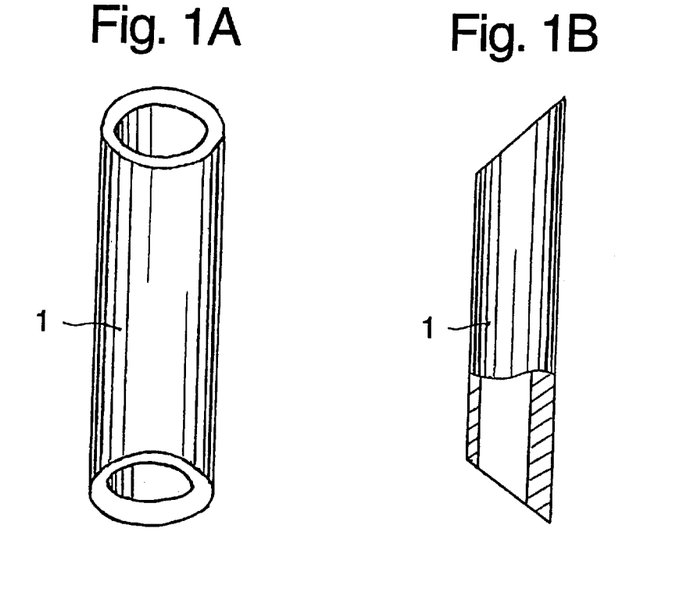
FIGS. 1A and 1B are a front view and a side view of an implant for an injured tendon of a digitus manus in accordance with this invention, respectively.

The implant 1 for an injured tendon of a digitus manus in accordance with the invention is, as shown in FIGS. 1A and 1B, a shape of a tube whose length is enough to surround a sutured portion of an injured tendon of a digitus manus. FIG. 1A shows a front view of the implant 1 and FIG. 1B shows a side view of the implant 1 and the lower half of which shows a cross sectional side view of the implant 1. The both ends of the implant 1 are cut slantly to form a trapezoid viewed from the side.

The implant 1 is made of a macromolecule polyvinyl alcohol family having characteristics of a long life to a living organism and a low reactivity to a foreign body, more specifically, macromolecule polyvinyl alcohol hydrogel (PVA-H). The implant 1 is a shape of a tube having a thin radial thickness whose bore diameter is such that an injured tendon of a digitus manus can be inserted into and passed through. More specifically, for example, the length of the upper side of the trapezoid is 10 mm, the length of the base side thereof is 14 mm, the outside diameter thereof is 4 mm, and the bore diameter thereof is 3 mm.

The material of which the implant 1 is made is macromolecule polyvinyl alcohol hydrogel (PVA-H) which is one of the macromolecule polyvinyl alcohol family having characteristics of a long life and a low reactivity to a foreign body and free from coalescence with its ambient living organism. The material also has characteristics of high hardwearing and good transparency. Each end of the implant 1 is cut slantly to form a trapezoid viewed from the side so as to facilitate a digitus manus whose tendon is injured to bend when the implant 1 is applied to cover the injured tendon. The upper side (shorter side) of the trapezoid is made to be thinner in a radial thickness than the base (longer side) thereof.

The implant 1 in accordance with the invention is used for a treatment, namely, an operation as shown below when a tendon of a digitus manus is injured. The process of the operation of the Zone 2 of an injured tendon of a digitus manus will now be described with reference to FIG. 4 through FIG. 9.

Figure 4:
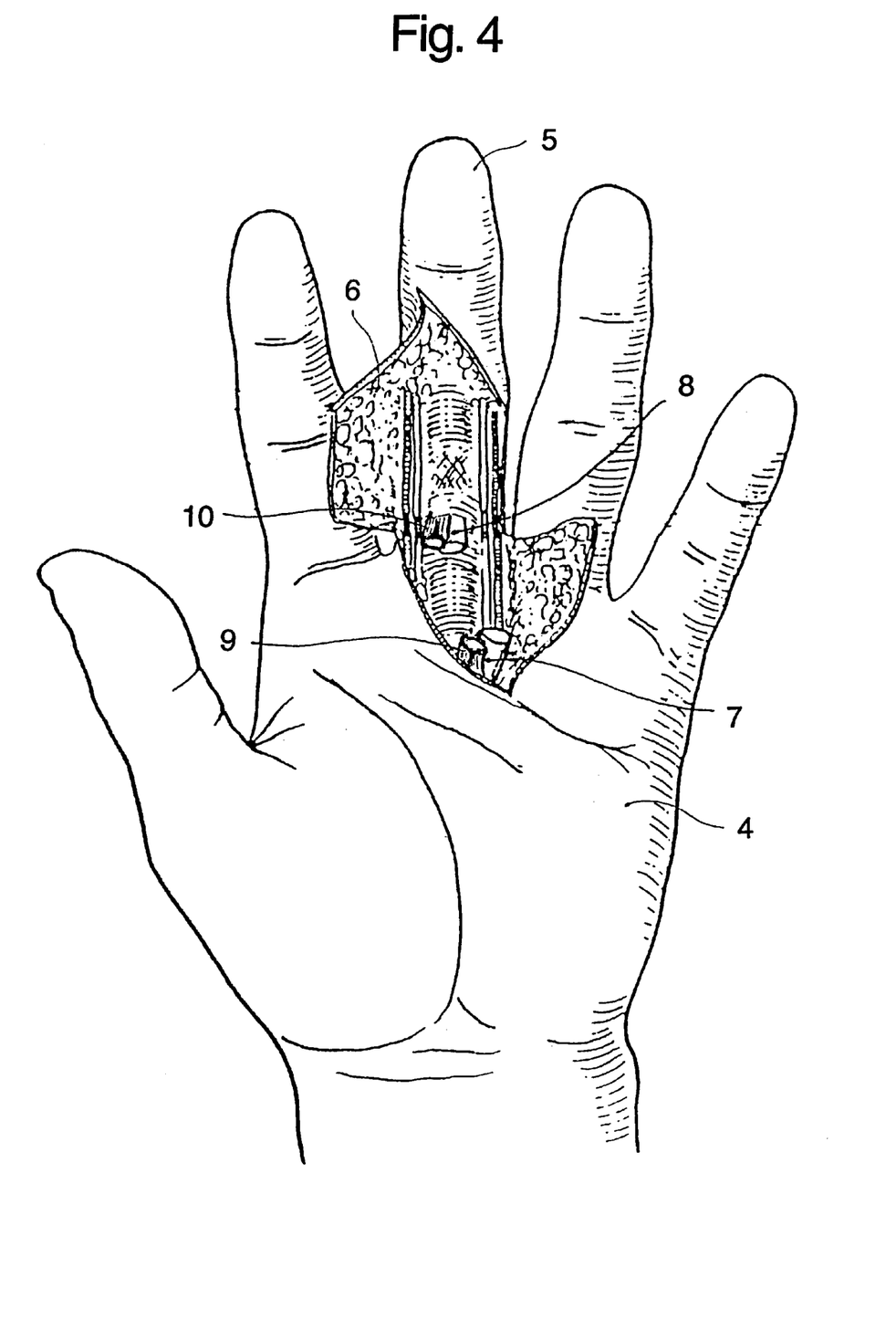
FIG. 4 is a view showing a status of an incised left palm whose tendon is injured.

FIG. 4 shows a step to prepare for the operation of suturing an injured tendon of the middle finger 5 of a left palm 4. First, incise the skin 6 of the finger 5 whose tendon is injured. FIG. 4 shows a finger tip side (the peripheral tendon) and a finger base side of a tendon which is amputated. The tendon consists of a flexor digitorum profundus muscle tendon and a flexor digitorum superficialis muscle tendon. 7 represents a finger base side of the flexor digitorum profundus muscle tendon. 8 represents a finger tip side of the flexor digitorum profundus muscle tendon. 9 represents a finger base side of the flexor digitorum superficialis muscle tendon. 10 represents a finger tip side of the flexor digitorum superficialis muscle tendon. The flexor digitorum profundus muscle tendon 7, 8 and the flexor digitorum superficialis muscle tendon 9, 10 will shrink to go inside if they are left as they are. Therefore, for operation they should be drawn and fixed to avoid shrinkage.

Figure 5:
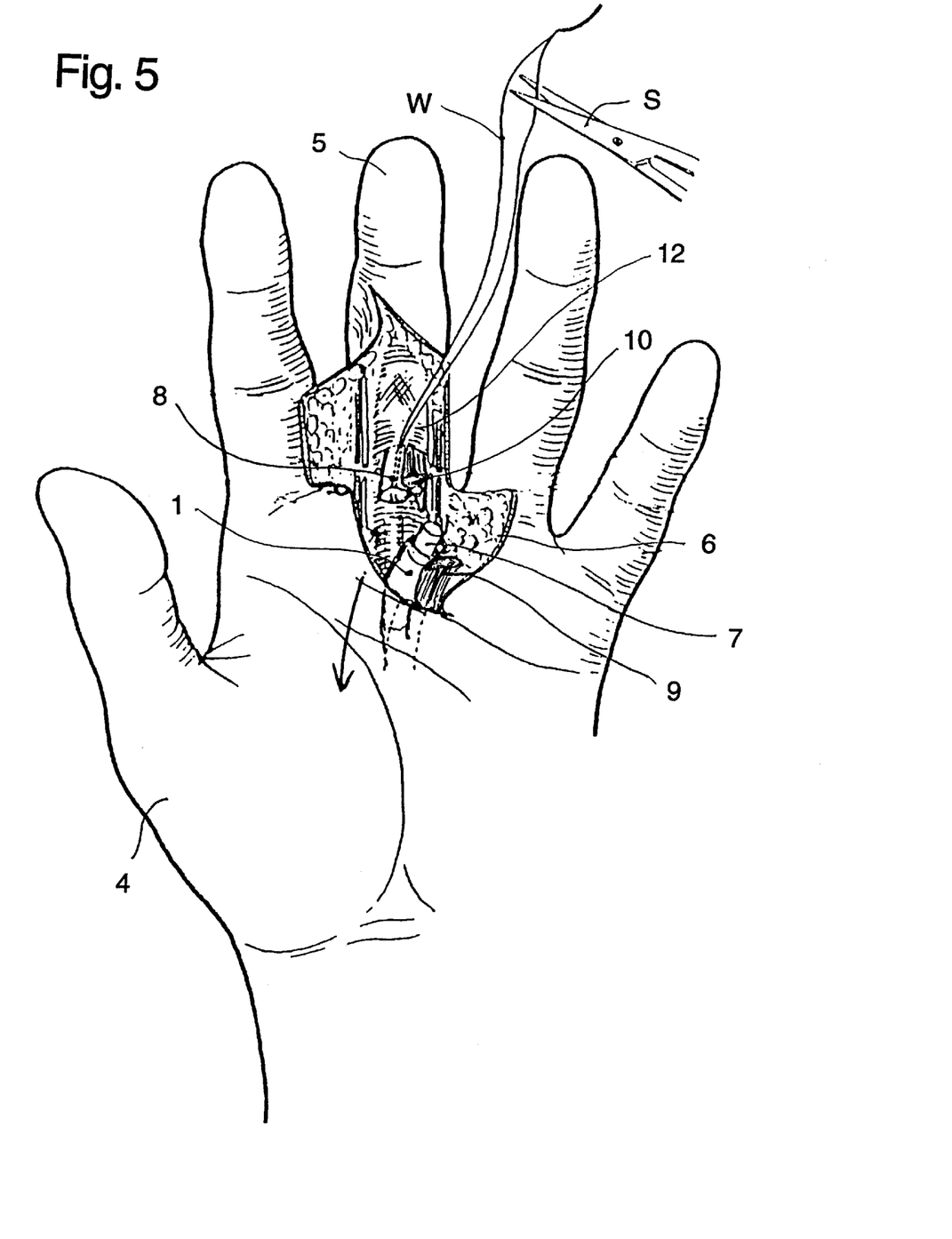
FIG. 5 is a view showing a status of the injured tendon of the left palm shown in FIG. 4 to which the implant is applied.
Figure 6:
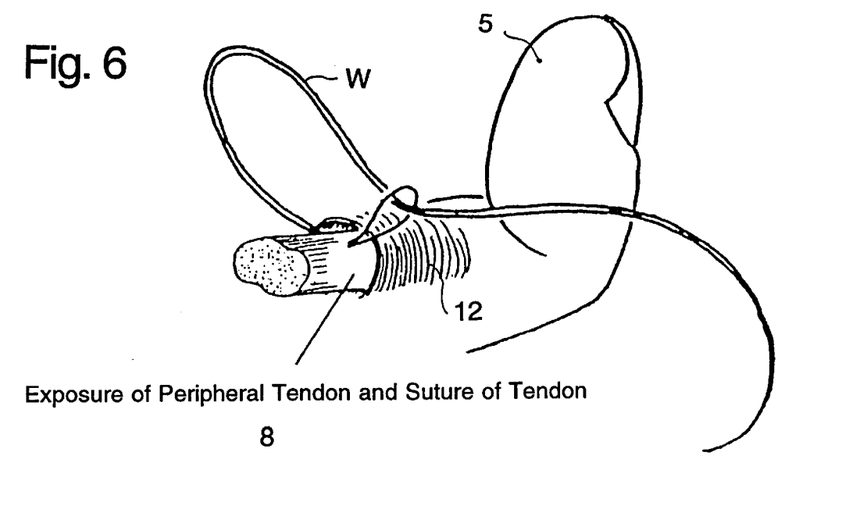
FIG. 6 is a magnified view showing a status of suturing the injured tendon shown in FIG. 4.
Figure 7:
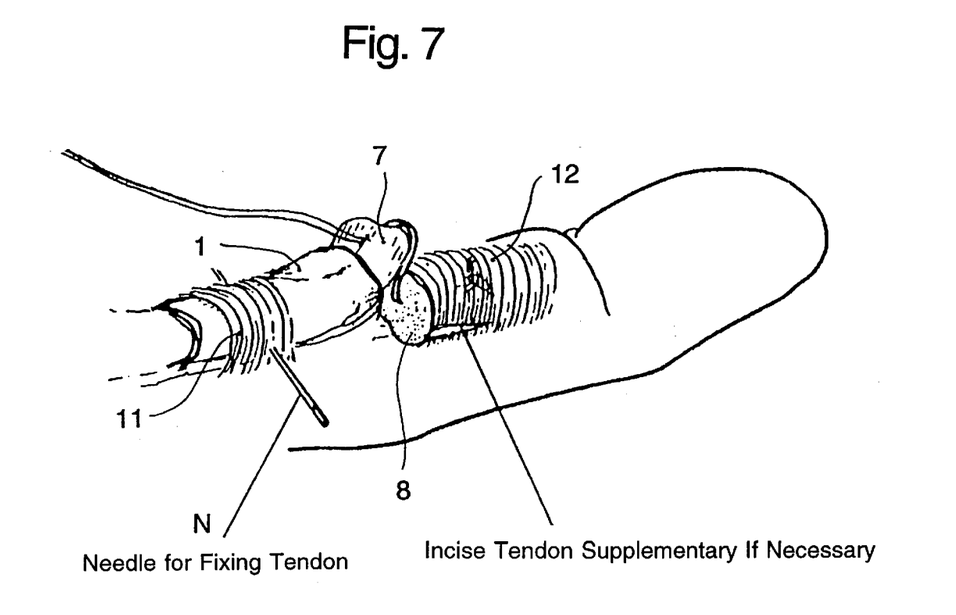
FIG. 7 is a magnified view showing a status of suturing the injured tendon shown in FIG. 4.

Next, as shown in FIG. 5 insert the implant 1 to fit over the finger base side of the flexor digitorum profundus muscle tendon 7 toward the center of the flexor digitorum profundus muscle tendon 7. Since the implant 1 is a tube into which the flexor digitorum profundus muscle tendon 7 can be inserted and passed through, the flexor digitorum profundus muscle tendon 7 is surrounded by the implant 1 as shown in FIG. 5. Then the operation to suture the injured tendon is to be started. Each of 11 and 12 represents a tendon sheath. Draw the tendon sheath 12 toward the finger tip side in order to expose the finger tip side of the flexor digitorum profundus muscle tendon 8. Then suture the finger tip side of the flexor digitorum profundus muscle tendon 8 with a thread W by means of a needle. FIG. 6 shows an enlarged view of this. In order to prevent the finger base side of the flexor digitorum profundus muscle tendon 7 from going inside of the tendon sheath 11, the finger base side of the flexor digitorum profundus muscle tendon 7 is fixed to the tendon sheath 11 by means of a needle N as shown in FIG. 7. Next suture the finger base side of the flexor digitorum profundus muscle tendon 7 to the finger tip side of the flexor digitorum profundus muscle tendon 8 with the thread W. The finger tip side of the flexor digitorum profundus muscle tendon 8 can be supplementary incised if more secure suture is necessary.

Figure 8:
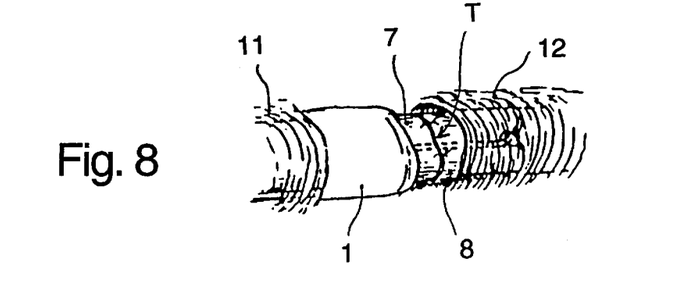
FIG. 8 is a view showing a status of suturing the injured tendon shown in FIG. 4 to which the implant is applied.
Figure 9:
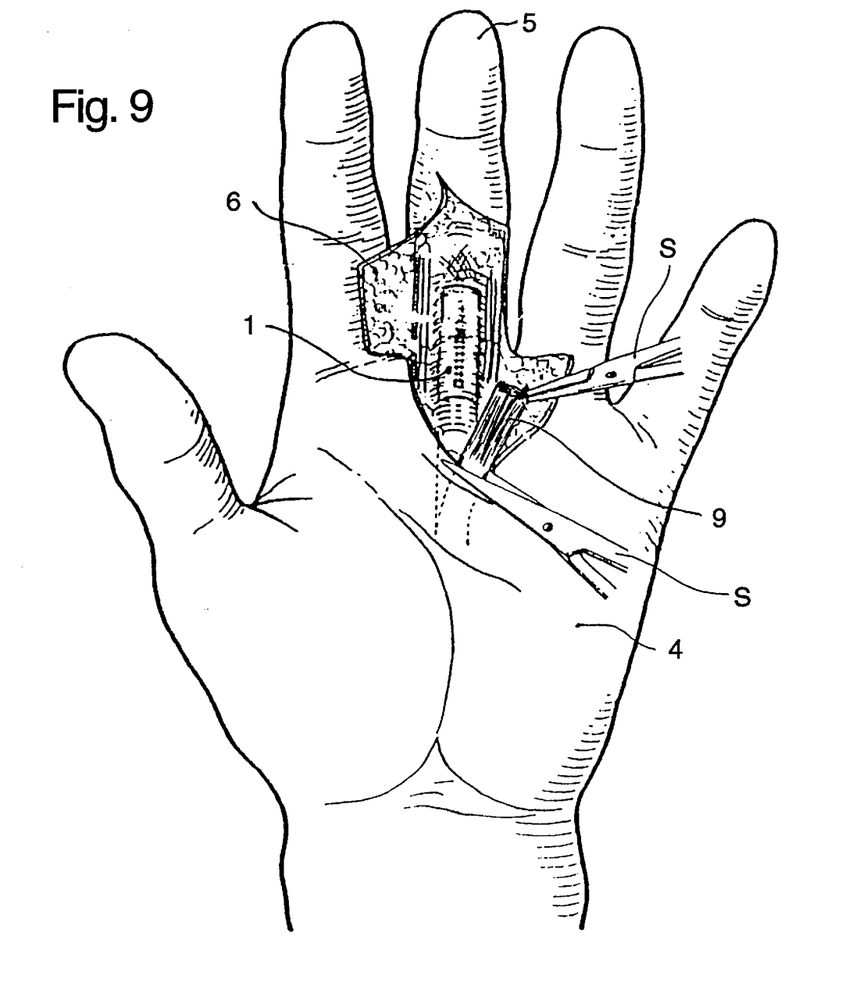
FIG. 9 is a view showing a status of completing the operation of suturing the injured tendon shown in FIG. 4.
Figure 10A:
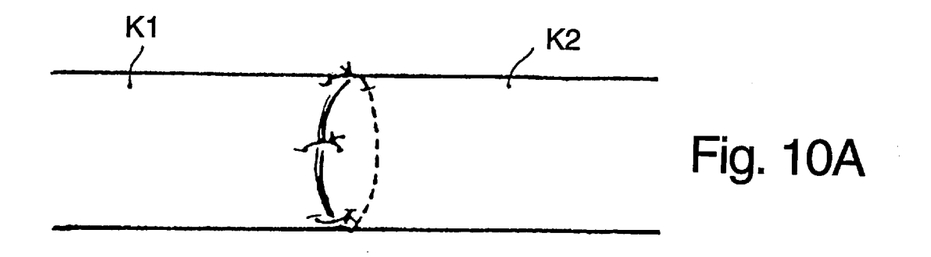
FIGS. 10A, 10B, 10C, and 10D are schematic views showing each operational procedure of suturing an injured tendon of a digitus manus.
Figure 10B:
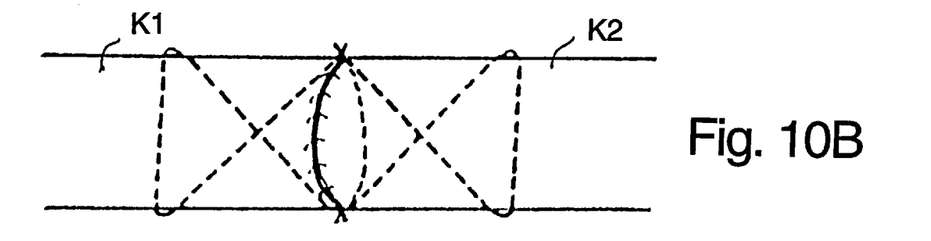
Figure 10C:
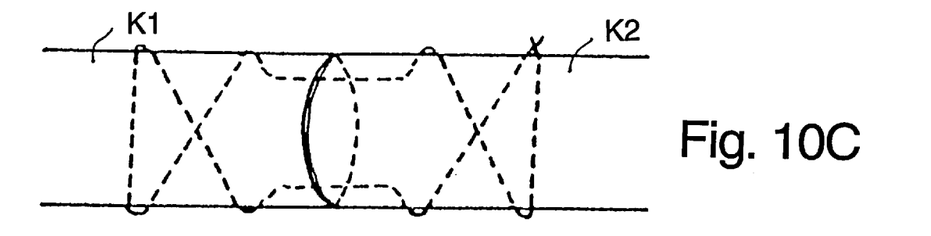
Figure 10D:
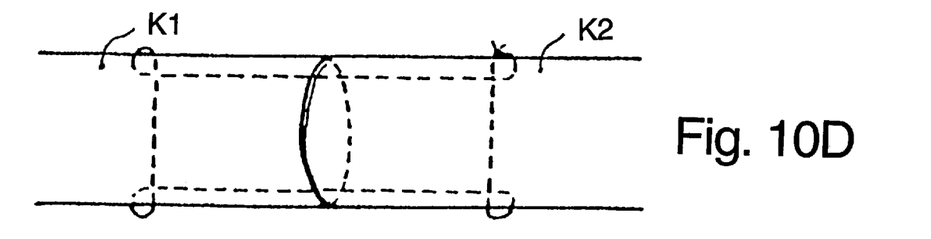
Figure 11A:
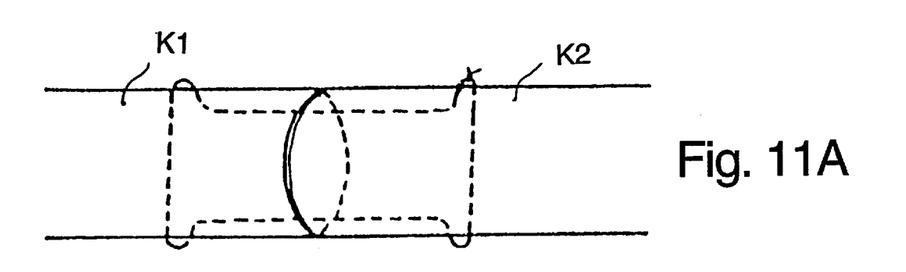
FIG. 11A, 11B, 11C and 11D are schematic views showing each operational procedure of suturing an injured tendon of a digitus manus.
Figure 11B:
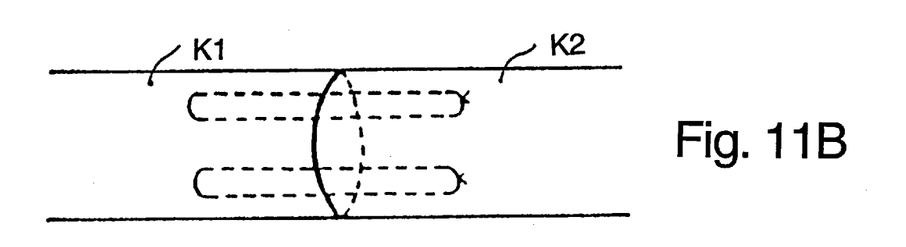
Figure 11C:
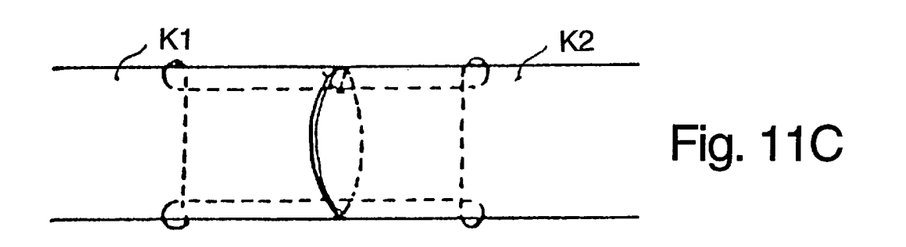
Figure 11D:
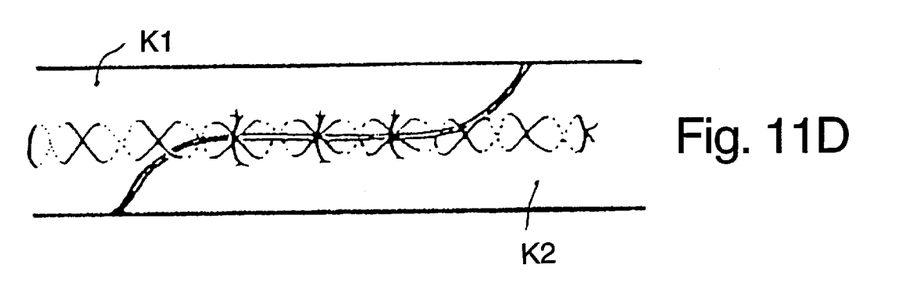

After both ends of the flexor digitorum profundus muscle tendon 7, 8 are sutured as shown in FIG. 8, move the implant 1 so as to surround the sutured portion T to prevent the sutured portion T from coalescing with its ambient living organism such as skins. FIG. 9 shows a status after the implant 1 has been moved to surround the sutured portion T. Then leave both ends of the flexor digitorum superficialis muscle tendon 9, 10 as they are and suture the skin which has been incised before. Then the operation is completed. S in FIGS. 5 and 9 represents a pair of scissors for operation.

The implant for an injured tendon of a digitus manus provided by the present claimed invention consists of a tube-shaped body made of a macromolecule polyvinyl alcohol family having characteristics of a long life to a living organism and a low reactivity to a foreign body. The above-mentioned macromolecule polyvinyl alcohol hydrogel (PVA-H) is most preferable as the material of which the implant is made, "a macromolecule polyvinyl alcohol family having characteristics of a long life to a living organism and a low reactivity to a foreign body". The reason of this is that PVA-H has following characteristics.
1) PVA-H rarely causes deterioration due to characteristics of a long life physically and organically and has a low reactivity to a foreign body.
2) The surface of PVA-H is smooth and has small coefficient of dynamic friction to other soft tissue and hard to wear out due to high moisture content.
3) PVA-H has characteristics of non-hygroscopicity and non-solubility in spite of high moisture content.
4) PVA-H has micropores on its surface which do not permeate macromolecule such as fibroblast or macrophage and permeate low-molecule such as protein or carbohydrate.

Due to the above-mentioned characteristics necessary nutrient can permeate through the implant and be taken to the injured portion of the tendon, while unnecessary infiltration of inflammatory cell can be prevented, thereby to promote healing the injured portion of the tendon.

The present claimed invention is an implant for an injured tendon of a digitus manus. Since a human body consists of a lot of tendons, it is very likely a tendon gets injured. Especially injuries of a tendon of a digitus manus happen very often. However, all injuries of a tendon of a digitus manus can not be treated by a specialist. In view of the above situation, the implant of the present claimed invention is preferable.

Figure 2:
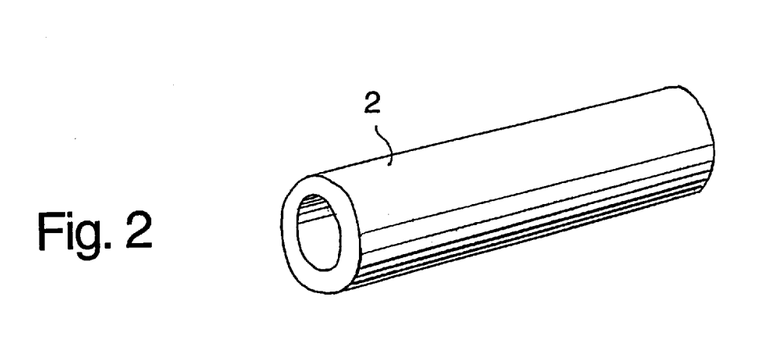
FIG. 2 is a perspective view of another preferred embodiment of the implant.
Figure 3:
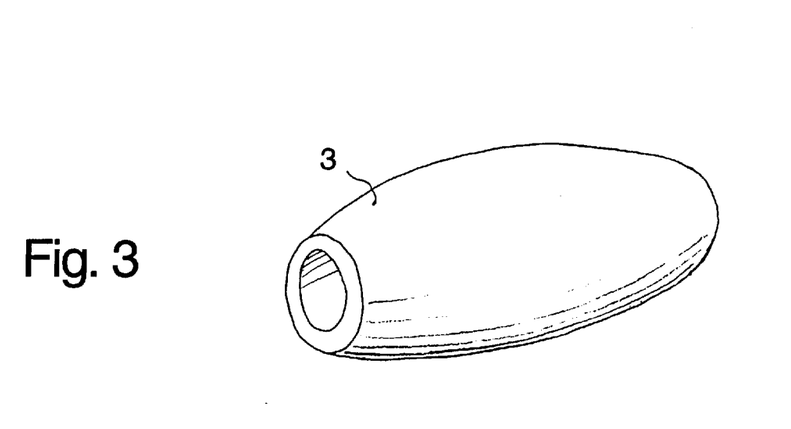
FIG. 3 is a perspective view of further different preferred embodiment of the implant.

The invention is not limited to the above-mentioned embodiments, but there may be various modifications without departing from the spirit or essential characteristics thereof such as: The material of which the implant is made is not limited to the above-mentioned polyvinyl alcohol hydrogel (PVA-H) but may include "material of a macromolecule polyvinyl alcohol family having characteristics of a long life to a living organism and a low reactivity to a foreign body" which exists present or may be developed in future. More specifically, the material includes general macromolecule from vinyl chloride to vinyl alcohol. The shape of the implant is not limited to a trapezoid viewed from the side as shown in FIG. 1 but may be an ordinal tube as shown in FIG. 2 or a cylinder with a diameter of its central part bigger than that of the other part as shown in FIG. 3. The cross section of the tube may be oval. The tube is not limited to be transparent, but may be semi-transparent or opaque. The implant provided by the present claimed invention includes all of the above-mentioned modification of the embodiments.

Followings are the summary of the invention.
1) The implant for an injured tendon of a digitus manus comprising a tube-shaped body made of a macromolecule polyvinyl alcohol family having characteristics of a long life to a living organism and a low reactivity to a foreign body characterized by that an injured tendon of a digitus manus is inserted into and passed through inside of the implant so as to function for suture and cure of the injured tendon, and for convalescence such as preventing the sutured tendon from coalescing with its ambient living organism.
2) The implant for an injured tendon of a digitus manus comprising a tube-shaped body made of macromolecule polyvinyl alcohol hydrogel characterized by that an injured tendon of a digitus manus is inserted into and passed through inside of the implant so as to function for suture and cure of the injured tendon, and for convalescence such as preventing the sutured tendon from coalescing with its ambient living organism.

What is claimed is:

1. An implant for repair of an injured tendon of a digitus manus, comprising a tube-shaped body having opposite ends angled obliquely such that said tube-shaped body has, viewed from a side, a trapezoidal shape, said tube-shaped body being made of a material selected from the family consisting of macromolecule polyvinyl alcohols, said implant being sized and configured to allow an injured tendon of a digitus manus to be inserted and passed therethrough, said implant facilitating suture of the injured tendon and convalescence, while avoiding coalescing of the sutured tendon with ambient living organisms.

2. An implant according to claim 1, wherein said material of the tube-shaped body is a macromolecule polyvinyl alcohol hydrogel.

3. An implant according to claim 1, wherein said tube-shaped body has a circular cross-section.

4. An implant according to claim 1, wherein said tube-shaped body is substantially transparent.

5. An implant according to claim 1, wherein said tube-shaped body has a radial wall thickness at a short side of the trapezoidal shape which is less than a radial wall thickness at an opposite long side of the trapezoidal shape.

6. An implant according to claim 5, wherein a ratio of a length of said short side to a length of said opposite long side is approximately 5/7.

* * * * *